(12) United States Patent
Zhu et al.

(10) Patent No.: US 11,311,408 B2
(45) Date of Patent: Apr. 26, 2022

(54) AUXILIARY SHAPING DEVICE FOR CERVICAL VAGINAL PENETRATION PLASTY AND USE METHOD THEREOF

(71) Applicant: Lan Zhu, Beijing (CN)

(72) Inventors: Lan Zhu, Beijing (CN); Honghui Shi, Beijing (CN)

(*) Notice: Subject to any disclaimer, the term of this patent is extended or adjusted under 35 U.S.C. 154(b) by 0 days.

(21) Appl. No.: 16/924,236

(22) Filed: Jul. 9, 2020

(65) Prior Publication Data

US 2020/0337890 A1   Oct. 29, 2020

(51) Int. Cl.
*A61F 6/08*   (2006.01)
*A61F 6/12*   (2006.01)

(52) U.S. Cl.
CPC . *A61F 6/08* (2013.01); *A61F 6/12* (2013.01)

(58) Field of Classification Search
CPC .... A61F 6/18; A61F 6/225; A61F 6/14; A61F 6/146; A61F 6/06; A61F 6/12; A61F 6/22; A61F 2002/30092; A61F 2/0022; A61F 2/94; A61F 2/95; A61F 13/472; A61F 2/005; A61F 5/4553; A61F 6/00; A61F 6/08; A61F 6/20; A61F 6/16; A61F 6/144; A61F 2/06; A61F 13/15; A61K 9/0034
See application file for complete search history.

(56) References Cited

U.S. PATENT DOCUMENTS

| 3,952,737 A * | 4/1976 | Lipfert | A61F 6/08 128/837 |
| 6,923,185 B1 * | 8/2005 | Koch | A61F 6/08 128/830 |

\* cited by examiner

*Primary Examiner* — Ophelia A Hawthorne

(57) ABSTRACT

An auxiliary shaping device for cervical vaginal penetration plasty and a use method thereof. The auxiliary shaping device includes a uterine cavity support, a cervical canal support and a vaginal support which are made of elastic material. The uterine cavity support is a hollow bowl-shaped structure; the uterine cavity support includes a first end and a second end; the first end has a larger diameter than the second end; the first end includes a plurality of valve bodies evenly distributed in circumferential direction; a concave part is arranged between two adjacent valve bodies, the concave part has an opening shape; uterine cavity secretions enter an interior of the uterine cavity support through the concave part; one end of cervical canal support is connected with the second end, other end is connected with vaginal support; a passage is arranged in the uterine cavity support; cervical canal support and vaginal support.

7 Claims, 1 Drawing Sheet

AUXILIARY SHAPING DEVICE FOR CERVICAL VAGINAL PENETRATION PLASTY AND USE METHOD THEREOF

TECHNICAL FIELD

The present invention relates to the technical field of medical instruments, and more particularly relates to an auxiliary shaping device for a cervical vaginal penetration plasty and a use method thereof.

BACKGROUND

Congenital no-vaginal cervical atresia (commonly known as: a woman with a hypoplastic vagina) is a disease of abnormal development of adolescent female reproductive tract, which not only makes it impossible to have normal sex life, but also seriously affects physical and mental health because menstrual blood cannot be discharged, causing obstruction and diseases of infection and endometriosis. At present, a cervical vaginal penetration plasty for preserving the fertility is a main treatment method, and the surgical technology is increasingly mature. However, obstruction caused by postoperative cervical adhesion is the most common clinical thorny complication, and most patients are forced to undergo hysterectomy. An auxiliary shaping device is a main measure for preventing such complication. The device can be fixed on the abdomen with a special fixing belt during use to prevent slippage. The inert and non-deformable material is used to meet the requirements of long-term placement after clinical operation.

At present, such device does not exist clinically and is often replaced by a drainage tube made of rubber material and an intrauterine device of metal material, which are easy to drop and infect after repeated placement. Aging of the rubber material causes middle cavity occlusion and obstruction. The placement of metal foreign objects causes it impossible for sex life and uncomfortable feeling.

Therefore, how to design an auxiliary shaping device capable of avoiding cervical adhesion after a cervical vaginal penetration plasty, reducing the use discomfort of patients and reserving the fertility function of adolescent girls, and a use method thereof is an important problem to be urgently solved in the field.

SUMMARY

In view of this, the present invention provides an auxiliary shaping device for a cervical vaginal penetration plasty capable of avoiding cervical adhesion after a cervical vaginal penetration plasty, reducing the use discomfort of patients, reserving the fertility function of adolescent girls and facilitating insertion and removal, and a use method thereof.

To achieve the above purpose, the present invention adopts the following technical solution:

An auxiliary shaping device for a cervical vaginal penetration plasty comprises a uterine cavity support, a cervical canal support and a vaginal support which are made of elastic material.

The uterine cavity support is a hollow bowl-shaped structure, the uterine cavity support includes a first end and a second end; and the first end has a larger diameter than the second end; the first end includes a plurality of valve bodies evenly distributed in circumferential direction; a concave part is arranged between two adjacent valve bodies, and the concave part has an opening shape; uterine cavity secretions enter the interior of the uterine cavity support through the concave part.

One end of the cervical canal support is connected with the second end, and the other end of the cervical canal support is connected with the vaginal support.

A passage is arranged in the uterine cavity support, the cervical canal support and the vaginal support. The passage communicates inner cavities of the uterine cavity support, the cervical canal support and the vaginal support, and the uterine cavity secretions are discharged along the passage.

By adopting the above technical solution, the present invention has the following beneficial effects: the uterine cavity support, the cervical canal support and the vaginal support have elasticity in the present invention, and can produce large deformation under the action of an external force, which facilitates the insertion and removal of the auxiliary shaping device, Meanwhile, the structure of the uterine cavity support has good spreading force and strength, which ensures that the uterine cavity support does not come out from a cervix, without fixation with a fixing belt, thereby reducing patient discomfort. Liquid discharged from a uterus can be discharged through the internal spaces of the uterine cavity support, the cervical canal support and the vaginal support to avoid obstruction and infection.

Preferably, an ejector rod is put into the passage; the center of an inner wall of the first end has a pushing part protruding outward; the ejector rod is abutted against the inner side of the pushing part; and the ejector rod supports the pushing part to insert the auxiliary shaping device smoothly.

Preferably, the inner wall of the pushing part is provided with a groove for placing the ejector rod; and the arrangement of the groove prevents the ejector rod from deviating from the pushing part, making the process of inserting the auxiliary shaping device smoother.

Preferably, the cervical canal support and the vaginal support are cylindrical, and the diameter of the vaginal support is larger than the diameter of the cervical canal support.

Preferably, a connection part between the cervical canal support and the vaginal support has a trapezoidal connecting part; and one end of the connecting part with a small caliber is connected with the cervical canal support, and one end with a large caliber is connected with the vaginal support. The cervical canal support and the vaginal support are in transitional variable-diameter connection through the connecting part; which can ensure that the cervical canal support is stuck in the cervix and may not slip into the uterus to ensure the successful shaping of the cervix.

Preferably, the uterine cavity support, the cervical canal support and the vaginal support are made of any one of silicone rubber, rubber, PVC and polyurethane. The above materials have high elastic modulus and good supporting force, and also have good biological compatibility.

A use method of an auxiliary shaping device for a cervical vaginal penetration plasty specifically comprises the following steps:

1) selecting an ejector rod: placing the ejector rod into the cervical canal support and the uterine cavity support in sequence along the passage of the vaginal support; and placing the end part of the ejector rod in the groove of the pushing part;

2) after connecting the ejector rod with the auxiliary shaping device, inserting the auxiliary shaping device under the driving of the ejector rod, wherein the uterine cavity support is placed in the uterus; the cervical canal support is placed in the cervix; the vaginal support is placed in the vagina; and then the ejector rod is pulled out to complete the insertion of the auxiliary shaping device;

3) when the auxiliary shaping device needs to be taken out, directly pulling the vaginal support at the vagina to take out the auxiliary shaping device.

Preferably, the ejector rod comprises: a pulling part and a supporting part; the supporting part is placed in the passage in a cylindrical shape; and the pulling part is placed outside the passage for inserting or withdrawing the ejector rod.

It can be known form the above technical solution that compared with the prior art, the present invention provides an auxiliary shaping device for a cervical vaginal penetration plasty and a use method thereof; and has the following beneficial effects:

(1) The uterine cavity support, the cervical canal support and the vaginal support in the present invention have elasticity, and can produce large deformation under the action a the external force, which facilitates the insertion and removal of the auxiliary shaping device.

(2) The structure of the uterine cavity support has good spreading force and strength, which ensures that the uterine cavity support does not come out from a cervix, without fixation with a fixing belt, thereby reducing patient discomfort.

(3) The cervical canal support is arranged behind the uterine cavity support, which can open the shaped cervix to ensure that the shaped cervix is not adhered and closed, thereby achieving the purpose of cervix shaping.

(4) The cervical canal support and the vaginal support are in transitional variable-diameter connection, which can ensure that the cervical canal support is stuck in the cervix and may not slip into the uterus to ensure the successful shaping of the cervix.

DESCRIPTION OF DRAWINGS

To more clearly describe the technical solution in the embodiments of the present invention or, in the prior art, the drawings required to be used in the description of the embodiments or the prior art will be simply presented below. Apparently, the drawings in the following description are merely the embodiments of the present invention, and for those ordinary skilled in the art, other drawings can also be obtained according to the provided drawings without contributing creative labor.

Figure 1:
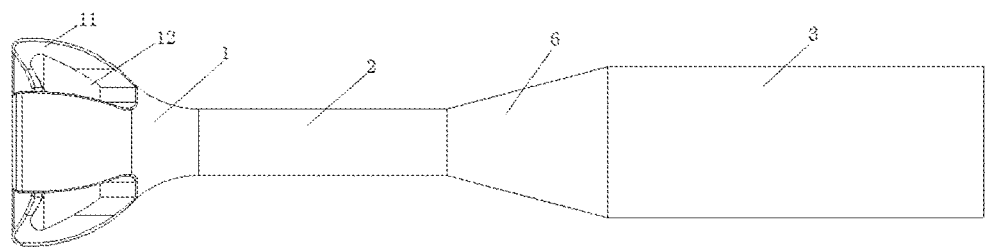
FIG. 1 is a structural schematic diagram of an auxiliary shaping device provided by the present invention.
Figure 2:
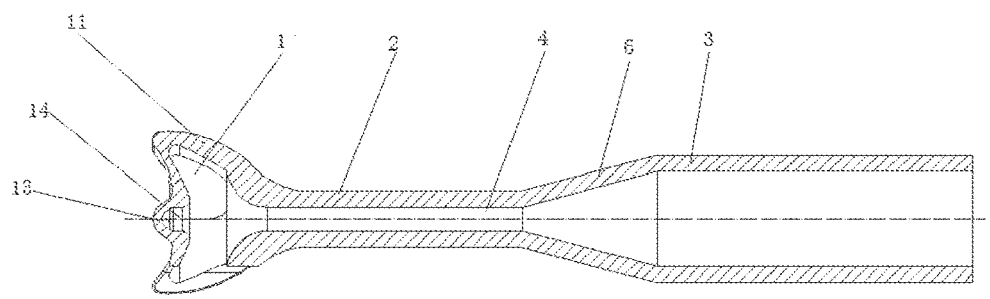
FIG. 2 is a sectional view of an auxiliary shaping device provided by the present invention.
Figure 3:
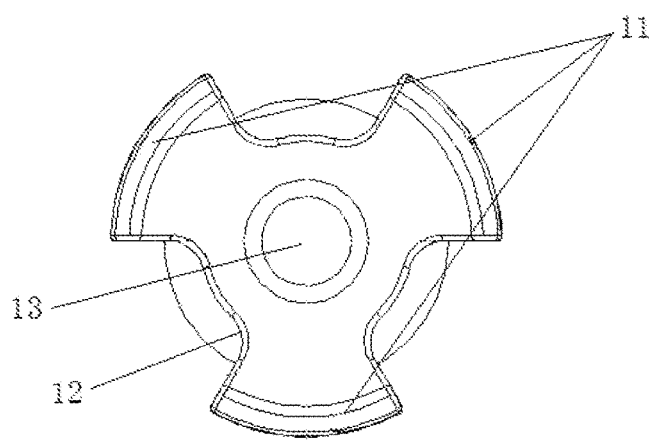
FIG. 3 is a top view of an auxiliary shaping device provided by the present invention.

In the figures,

1—uterine cavity support;
11—valve body; 12—concave part; 13—pushing part; 14—groove;
2—cervical canal support; 3—vaginal support; 4—passage;
5—ejector rod;
51—pulling part; 52—supporting part;
6—connecting part.

DETAILED DESCRIPTION

The technical solution in the embodiments of the present invention will be clearly and fully described below in combination with the drawings in the embodiments of the present invention. Apparently, the described embodiments are merely part of the embodiments of the present invention, not all of the embodiments. Based on the embodiments in the present invention, all other embodiments obtained by those ordinary skilled in the art without contributing creative labor will belong to the protection scope of the present invention.

Embodiments of the present invention disclose an auxiliary shaping device for a cervical vaginal penetration plasty, comprising a uterine cavity support 1, a cervical canal support 2 and a vaginal support 3 which are made of elastic material.

The uterine cavity support 1 is a hollow bowl-shaped structure, the uterine cavity support 1 includes a first end and a second end; and the first end has a larger diameter than the second end; and the first end includes three valve bodies 11 evenly distributed in circumferential direction; a concave part 12 is arranged between two adjacent valve bodies 11 and the concave part 12 has an opening shape; and uterine cavity secretions enter the interior of the uterine cavity support 1 through the concave part 12.

One end of the cervical canal support 2 is connected with the second end, and the other end of the cervical canal support 2 is connected with the vaginal support 3.

Figure 4:
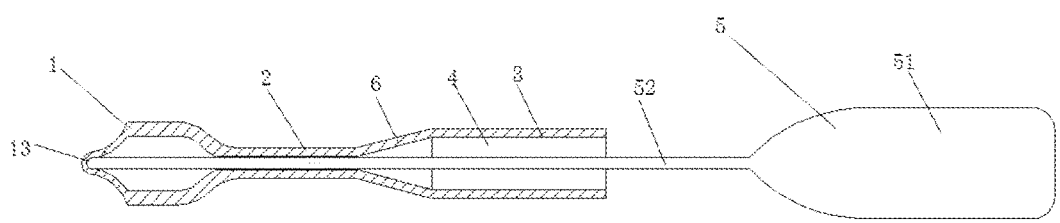
FIG. 4 is a schematic diagram of shape change of an auxiliary shaping device which is inserted by an ejector rod provided by the present invention.

A passage 4 is arranged in the uterine cavity support 1, the cervical canal support 2 and the vaginal support 3. The passage 4 communicates inner cavities of the uterine cavity support 1, the cervical canal support 2 and the vaginal support 3, and the uterine cavity secretions are discharged along the passage 4. As shown in FIG. 4, under the action of an ejector rod 5, the auxiliary shaping device is deformed and inserted: and after the uterine cavity support 1 is inserted. the rebound, the own structural strength and the supporting force can be used to avoid the auxiliary shaping device from dropping from the cervix.

To further optimize the above technical solution, the ejector rod 5 is put into the passage 4; the center of an inner wall of the first end has a pushing part 13 protruding outward; and the ejector rod 5 is abutted against the inner side of the pushing part 13.

To further optimize the above technical solution, the inner wall of the pushing part 13 is provided with a groove 14 for placing the ejector rod 5.

To further optimize the above technical solution, the cervical canal support 2 and the vaginal support 3 are cylindrical, and the diameter of the vaginal support 3 is larger than the diameter of the cervical canal support 2.

To further optimize the above technical solution, a connection part between the cervical canal support 2 and the vaginal support 3 has a trapezoidal connecting part 6; and one end of the connecting part 6 with a small caliber is connected with the cervical canal support 2, and one end with a large caliber is connected with the vaginal support 3. The uterine cavity support 1, the cervical canal support 2, the vaginal support 3 and the connecting part 6 are of an integral structure.

To further optimize the above technical solution, the uterine cavity support 1, the cervical canal support 2 and the vaginal support 3 are made of any one of silicone rubber, rubber, PVC and polyurethane.

A use method of an auxiliary shaping device for a cervical vaginal penetration plasty specifically comprises the following steps:

1) selecting an ejector rod 5; placing the ejector rod 5 into the cervical canal support 2 and the uterine cavity support 1 in sequence along the passage 4 of the vaginal support 3; and placing the end part of the ejector rod 5 in the groove 14 of the pushing part 13;

2) after connecting the ejector rod 5 with the auxiliary shaping device, inserting the auxiliary shaping device under the driving of the ejector rod 5, wherein the uterine cavity support 1 is placed in the uterus; the cervical canal support 2 is placed in the cervix; the vaginal support 3 is placed in the vagina; and then the ejector rod 5 is pulled out to complete the insertion of the auxiliary shaping device;

3) when the auxiliary shaping device needs to be taken out, directly pulling the vaginal support 3 at the vagina to take out the auxiliary shaping device.

To further optimize the above technical solution, the ejector rod 5 comprises: a pulling part 51 and a supporting part 52; the supporting part 52 is placed in the passage 4 in a cylindrical shape; and the pulling part 51 is placed outside the passage 4 for inserting or withdrawing the ejector rod 5.

Each embodiment in the description is described in a progressive way. The difference of each embodiment from each other is the focus of explanation. The same and similar parts among all of the embodiments can be referred to each other. For the device disclosed by the embodiments, because the device corresponds to a method disclosed by the embodiments, the device is simply described. Refer to the description of the method part for the related part.

The above description of the disclosed embodiments enables those skilled in the art to realize or use the present invention. Many modifications to these embodiments will be apparent to those skilled in the art. The general principle defined herein can be realized in other embodiments without departing from the spirit or scope of the present invention. Therefore, the present invention will not be limited to these embodiments shown herein, but will conform to the widest scope consistent with the principle and novel features disclosed herein.

The invention claimed is:

1. An auxiliary shaping device for a cervical vaginal penetration plasty, comprising a uterine cavity support, a cervical canal support and a vaginal support which are made of elastic material, wherein
    the uterine cavity support is a hollow bowl-shaped structure, the uterine cavity support comprises a first end and a second end; and the first end has a larger diameter than the second end; the first end comprises a plurality of valve bodies evenly distributed in circumferential direction; a concave part is arranged between two adjacent valve bodies, and the concave part has an opening shape; and uterine cavity secretions enter an interior of the uterine cavity support through the concave part;
    one end of the cervical canal support is connected with the second end, and an other end of the cervical canal support is connected with the vaginal support;
    a passage is arranged in the uterine cavity support, the cervical canal support and the vaginal support; the passage communicates inner cavities of the uterine cavity support, the cervical canal support and the vaginal support, and the uterine cavity secretions are discharged along the passage;
    an ejector rod is put into the passage; the first end has a pushing part protruding outward; and the ejector rod is abutted against an inner side of the pushing part.

2. The auxiliary shaping device for the cervical vaginal penetration plasty according to claim 1, wherein the cervical canal support and the vaginal support are cylindrical, and a diameter of the vaginal support is larger than a diameter of the cervical canal support.

3. The auxiliary shaping device for the cervical vaginal penetration plasty according to claim 2, wherein a connection part between the cervical canal support and the vaginal support is a trapezoidal connecting part; and one end of the trapezoidal connecting part is connected with the cervical canal support, and another end of the trapezoidal connecting part is connected with the vaginal support.

4. The auxiliary shaping device for the cervical vaginal penetration plasty according to claim 3, wherein the uterine cavity support, the cervical canal support and the vaginal support are made of any one of silicone rubber, rubber, PVC and polyurethane.

5. A use method of the auxiliary shaping device for the cervical vaginal penetration plasty of claim 1, comprising the following steps:
    1) selecting the ejector rod; placing the ejector rod into the cervical canal support and the uterine cavity support in sequence along the passage of the vaginal support; and placing an end part of the ejector rod in a groove of the pushing part;
    2) after connecting the ejector rod with the auxiliary shaping device, inserting the auxiliary shaping device under a driving of the ejector rod, wherein the uterine cavity support is placed in a uterus; the cervical canal support is placed in a cervix; the vaginal support (3) is placed in a vagina: and then the ejector rod is pulled out to complete an insertion of the auxiliary shaping device;
    3) when the auxiliary shaping device needs to be taken out, directly pulling the vaginal support at the vagina to take out the auxiliary shaping device.

6. The use method of the auxiliary shaping device for the cervical vaginal penetration plasty according to claim 5, wherein the ejector rod comprises: a pulling part and a supporting part; the supporting part is in a cylindrical shape and placed in the passage; and the pulling part is placed outside the passage for inserting or withdrawing the ejector rod.

7. The auxiliary shaping device for the cervical vaginal penetration plasty according to claim 1, wherein an inner wall of the pushing part is provided with a groove for placing the ejector rod.

* * * * *